United States Patent
Bartsch (12)

(10) Patent No.: US 6,686,181 B1
(45) Date of Patent: Feb. 3, 2004

(54) METHOD FOR THE PRODUCTION OF L-AMINO ACIDS FROM THEIR RACEMIC N-ACEYTYL-D, L-DERIVATIVES BY ENZYMATIC RACEMATE CLEAVAGE BY MEANS OF ISOLATED RECOMBINANT ENZYMES

(75) Inventor: Klaus Bartsch, Königstein (DE)

(73) Assignee: Aventis Corporation GmbH, Frankfurt (DE)

( * ) Notice: Subject to any disclaimer, the term of this patent is extended or adjusted under 35 U.S.C. 154(b) by 0 days.

(21) Appl. No.: 10/031,356

(22) PCT Filed: Jun. 17, 2000

(86) PCT No.: PCT/EP00/05586

§ 371 (c)(1),
(2), (4) Date: Jan. 17, 2002

(87) PCT Pub. No.: WO01/05982

PCT Pub. Date: Jan. 25, 2001

(30) Foreign Application Priority Data

Jul. 20, 1999 (DE) .......................................... 199 33 362

(51) Int. Cl.⁷ .......................... C12P 13/04; C12P 13/24; C12P 13/22; C12P 13/14; C12P 13/06
(52) U.S. Cl. ...................... 435/106; 435/107; 435/108; 435/110; 435/116; 536/23.1; 536/23.2; 536/23.7; 536/24.1
(58) Field of Search ................................ 435/106, 110, 435/116, 108, 107, 69.1; 536/23.1, 23.2, 23.7, 24.1

(56) References Cited

U.S. PATENT DOCUMENTS

| | | |
|---|---|---|
| 6,177,616 B1 | 1/2001 | Bartsch et al. |
| 6,235,516 B1 | 5/2001 | Ghisalba et al. |

FOREIGN PATENT DOCUMENTS

| | | |
|---|---|---|
| DE | 43 08 061 A1 | 9/1994 |
| EP | 0 358 428 A2 | 3/1990 |
| GB | 2031896 A | 4/1980 |

*Primary Examiner*—Herbert J. Lilling
(74) *Attorney, Agent, or Firm*—Frommer Lawrence & Haug LLP

(57) ABSTRACT

Process for the preparation of L-amino acids from their racemic N-acetyl-D,L derivatives by enzymatic resolution by means of isolated, recombinant enzymes A process for the preparation of proteinogenic or nonproteinogenic L-amino acids, in particular L-phosphinothricin, from their racemic N-acetyl-D,L derivatives comprises
a) selectively deacetylating N-acetyl-L derivatives of the corresponding L-amino acids by an enzymatic resolution by means of isolated, recombinant enzymes, while N-acetyl-D derivatives of the corresponding D-amino acids are not deacetylated and
b) separating the deacetylated L-amino acids obtained preparatively from the nondeacetylated N-acetyl-D derivatives and/or the incompletely deacetylated N-acetyl-L derivatives.

11 Claims, No Drawings

METHOD FOR THE PRODUCTION OF L-AMINO ACIDS FROM THEIR RACEMIC N-ACEYTYL-D, L-DERIVATIVES BY ENZYMATIC RACEMATE CLEAVAGE BY MEANS OF ISOLATED RECOMBINANT ENZYMES

Process for the preparation of L-amino acids from their racemic N-acetyl-D,L derivatives by enzymatic resolution by means of isolated, recombinant enzymes.

The production of the nonproteinogenic amino acid L-PPT (L-phosphinothricin) by resolution with high purity and yield has previously only been described by cleavage of phenacetylphosphinothricin with penicillin G acylase from *Escherichia coli* (DE-A-3048612). The synthesis of phenacetyl-PPT, however, is more complicated and more expensive in comparison with N-Ac-PPT. However, penicillin G acylase has no specificity for aliphatic acyl radicals and thus also no specificity for N-Ac-PPT. Other known acylases likewise have no or only a low substrate specificity for N-Ac-PPT and have previously only been employed in microbial biotransformations without purification of the enzymes (as described, for example, in DE-A-2939269). On account of this, only very low space/time yields were achievable. The patent application EP-A-0382113 discloses the L-specific cleavage of N-Ac-PPT carboxylic acid esters by acylase 1. Even this enzyme, however, has no specificity for the free carboxylic acid and therefore necessitates esterification as an additional synthesis step in the preparation of the substrate.

The patent application DE-A-1 9652284 describes the specific isolation of microbial deacetylases from soil samples with specificity for N-acetylamino acids, preferably N-acetylphosphinothricin (N-Ac-PPT), and the cloning of the corresponding genes from Stenotrophomonas sp. and *Comamonas acidovorans*.

On account of the sequence homologies found and the substrate specificity tests carried out, it was possible to show that the deacetylases described belong to the group of hippurate hydrolases (EC 3.5.1.32), whose natural substrate is N-benzoylglycine, an amino acid derivative having an aromatic N-acyl function. It was therefore interesting that these enzymes can also accept N-acetylated amino acids, in particular N-acetylphosphinothricin, as a substrate, these being amino acid derivatives having aliphatic N-acyl functions. The patent applications DE-A-2939269 and DE-A-2717440 disclose that the herbicidal action of racemic phosphinothricin emanates from its L enantiomer (L-PPT) alone.

In this connection, it was interesting that the deacetylases found exclusively cleave the L-enantiomers of N-acetyl-PPT, and of N-acetyl derivatives of some proteinogenic amino acids, with high specificity. These enzymes are therefore excellently suited to the preparation of L-amino acids, in particular of the herbicidal active compound L-phosphinothricin, from their racemic N-acetyl derivatives according to the principle of resolution, as is described, for example, in the patent applications EP-A-0304021, DE-A-2939269 and DE-A-3048612. Significant disadvantages of the processes in the three patent applications described above, however, consist in the fact that (1) only low substrate concentrations (about 0.5% in the case of the patent application DE-A-2939269) can be employed, on account of which industrial suitability is to be assessed as low, that (2) reaction is carried out with nonisolated enzymes, on account of which the problems of side reactions and subsequent purification steps cannot be solved or can only be solved very cost-intensively and that (3) cost-intensive product preparation is necessary (as in the case of the patent application DE-A-3048612).

The object on which the invention is based lies in expressing one or more novel deacetylases (such as already characterized in DE-A-19652284) in a suitable form and amount, and in making it possible with the aid of these enzymes to prepare L-PPT and some proteinogenic L-amino acids from the chemically very easily accessible racemic N-acetyl-D,L derivatives by resolution with high yield and enantiomeric purity.

In the case in which the enzymatic activity is already approximately known, and in which cloning of the nucleic acid sequence encoding the enzyme has also already been carried out, the first operation consists in transferring the appropriate nucleic acid fragment to a suitable vector in order then either to carry out overproduction in a suitable bacterial strain, and/or in order to isolate the protein after the overexpression. The enzyme isolated in this way can either be used directly for the enzymatic reaction or else attached to a matrix by means of suitable coupling groups.

A first enzymatic test is advisable in order to obtain general confirmation as to whether the desired reaction is proceeding. All further steps serve to optimize the parameters with respect to the reaction specificity (based on starting material and product), the reaction rate, the reaction efficiency, the half-life of the enzyme employed, and the possible substrate concentrations. In the case that individual parameters do not correspond exactly to the requirements, one is able to carry out suitable changes to the nucleic acid sequence encoding the enzyme, which results in a further optimization of the natural enzyme present.

The cloning of individual deacetylases used has already been described in the application DE-A-1 9652284. The nucleic acid fragments coding for the appropriate deacetylases were recloned in the appropriate expression vectors as carried out further below in Example 1 in order thus to ensure a necessary extent of unequivocal substrate specificity and the absence of side reactions. Thus, although it was possible in the application DE-A-1 9652284 to show that N-acetyl-L-PPT is deacetylated, it was not possible to show that N-acetyl-D-PPT is not also deacetylated. The exclusive reaction of N-acetyl-L-amino acids and N-acetyl-L-PPT, however, is an elementary precondition for the industrial use intended here.

The invention relates to a process for the preparation of proteinogenic or nonproteinogenic L-amino acids from their racemic N-acetyl-D,L derivatives, which comprises
 (a) selectively deacetylating N-acetyl-L derivatives of the corresponding L-amino acids by an enzymatic resolution by means of isolated, recombinant enzymes, while N-acetyl-D derivatives of the corresponding D-amino acids are not deacetylated and
 (b) separating the deacetylated L-amino acids obtained preparatively from the nondeacetylated N-acetyl-D derivatives and/or the incompletely deacetylated N-acetyl-L derivatives.

The invention relates in particular to a process for the preparation of L-phosphinothricin (L-PPT) from N-acetyl-D,L-phosphinothricin by enzymatic resolution by means of isolated, recombinant enzymes.

The invention furthermore relates to a process for the preparation of L-glutamic acid, L-histidine, L-leucine, L-glutamine and/or L-phenylalanine from their corresponding N-acetyl-D,L derivatives by enzymatic resolution.

The invention furthermore relates to a process which comprises carrying out the enantioselective production of one or more L-amino acids from their corresponding racemic N-acetyl-D,L derivatives using one or more deacetylases from the group consisting of the hippurate hydrolases, and in particular carrying out the enantioselective production of L-phosphinothricin, L-glutamic acid, L-histidine, L-leucine, L-glutamine and/or L-phenylalanine from their corresponding racemic N-acetyl-D,L derivatives using one or more deacetylases from the group consisting of the hippurate hydrolases.

In particular, the invention relates to a process which comprises carrying out the enantioselective production of one or more L-amino acids from their corresponding racemic N-acetyl-D,L derivatives using the enzymes deac1 from Stenotrophomonas sp. and/or deac2 from *Comamonas acidovorans* (both deacetylases are described in DE-A-19652284), and in this context very particularly the processes which comprise carrying out the enantioselective production of L-phosphinothricin, L-glutamic acid, L-histidine, L-leucine, L-glutamine and/or L-phenylalanine from their corresponding racemic N-acetyl-D,L derivatives using the enzymes deac1 from Stenotrophomonas sp. or/and deac2 from *Comamonas acidovorans* (both deacetylases are described in DE-A-19652284). Both enzymes have a significant sequence homology, which results in an identical or at least similar function in the cleavage of N-acetyl-D,L derivatives.

In addition, the invention relates to the use of the recombinant deacetylases produced as biocatalysts which allow the appropriate reactions to be carried out using high substrate concentrations and/or with the attainment of high space/time yields, in particular using the recombinant deacetylases in immobilized form.

The invention furthermore relates to the carrying-out of the processes described above at reaction temperatures of approximately 25° C. to 65° C., preferably at reaction temperatures of approximately 30° C. to 45° C. and particularly preferably at reaction temperatures of approximately 35° C. to 40° C.

In addition, the invention relates to the carrying-out of the processes described above at substrate concentrations of approximately 10 mM to 1500 mM, preferably at substrate concentrations of greater than 50 mM, particularly preferably at substrate concentrations of greater than 250 mM and very particularly preferably at substrate concentrations of greater than 500 mM.

The invention furthermore relates to the separation of the L-amino acid or of the L-PTC produced with the aid of the steps described above from the corresponding N-acetyl-D,L derivatives, which have either not been reacted—as in the case of N-acetyl-D derivative—or not been completely reacted—as in the case of N-acetyl-L derivative.

In this context, utilizable processes are the use of ion-exchange chromatography on an acidic ion exchanger or else the extraction of the N-acetyl-D,L derivatives by means of an organic solvent, such as, for example, of methyl isobutyl ketone, the L-amino acid or the L-PTC produced above passing into the aqueous phase, from which it is then concentrated by drying.

EXAMPLES

1. Production of the Deac Enzyme as a Recombinant Protein in *Escherichia coli*

The deac1 structural gene from Stenotrophomonas sp., coding for an N-Ac-PPT-specific deacetylase, was cloned as a 1.4 kb BamHI/SalI fragment (described in DE-A-19652284) into the Bam HI/Sal I cleavage site of the His Tag expression vector pQE30 from Quiagen [Quiaexpress Kit, Type IV, Catalog No. 32149, Stuber et al. (1990), in Immunological Methods, Lefkovits, I. and Pemis, B., eds., Vol. IV, Academic Press, New York, pp.121–152].

All molecular-biological studies were carried out according to standard protocols, as described, for example, in Ausubel et al. (1995), Current protocols in molecular biology, John Wiley and Sons, New York. The religated construct was transformed in the bacterial strain *E. coli* M15 recommended by the manufacturer (Qiagen), and recombinant clones were selected on 100 $\mu$g/ml ampicillin and 25 $\mu$g/ml kanamycin. The expression of recombinant fusion protein was induced by addition of 1 mM IPTG. The cells were harvested 4–5 h after induction and stored at −20° C. until the working-up of the protein.

By means of SDS/polyacrylamide electrophoresis of cell aliquots of the induced clones, it was possible to detect the HisTag deac1 fusion protein as an additional band of 49 kDa.

The enzymatic activity of the deacetylase fusion protein was detected in a radioassay using [14 C]-N-acetyl-L-PPT as a substrate. For this, 200 $\mu$l each of the induced cultures were permeabilized at 37° C. with 0.5% toluene, 0.5% ethanol for 30 min. The cell pellets were then resuspended in 25 $\mu$l each of 0.1 mM [$^{14}$C]-N-acetyl-L-PPT, 10 mM NaCl, 10 mM Na phosphate, pH 7.5 and incubated at 37° C. for 1 h. For the qualitative determination of the [$^{14}$C]-L-PPT formed, 5 $\mu$l each of aliquots of the test batches were analyzed by thin-layer chromatography on HPTLC cellulose plates (Merck) using n-propanol:25% ammonia=3:2 as an eluent. The radioactive bands were made visible by autoradiography on X-ray film.

For the quantification of the enzyme reaction, the test batches were measured in radio-HPLC using Spherisorb® SAX as a separating column (eluent: 5 mM KH$_2$PO4, 10% methanol, pH=1.92, flow rate: 0.5 ml/min). Under these conditions, [$^{14}$C]-L-PPT eluted at 4.5 min and [$^{14}$C]-N-acetyl-L-PPT at 6.5 min.

The expression clone having the highest N-acetyl-L-PPT-specific deacetylase activity produces the deacetylase protein according to semiquantitative determination with a proportion of about 10% to the total protein and was used for the enzyme purification and the biotransformations described below.

2. Purification of the Deacetylase by Affinity Chromatography

The deacetylase protein was isolated from the expression strain pQEDEAC newly named according to the cloning described in Example 1 according to the Quiagen protocol (Qiaexpress kit) by affinity chromatography on nickel nitrilotriacetate matrix (Ni-NTA) under native conditions. For this, 800 ml of culture of the expression strain pQEDEAC were fermented and induced as described in Example 1. The harvested cell pellet (4 g) was resuspended in 20 $\mu$l of lysis buffer and disrupted using ultrasound. After centrifuging off, the clear protein lysate (120 mg of total protein) was treated with 4 ml of 50% strength Ni-NTA suspension for the binding of the HisTag fusion protein and the material was then loaded onto an enzyme column. The affinity matrix was washed with 10 volumes of wash buffer and then eluted with 4 ml of elution buffer. To check the affinity purification, aliquots of the cell disruption, of the wash solutions and of the eluate were analyzed by means of SDS/polyacrylamide gel electrophoresis. The deacetylase activity of the various protein-containing fractions was determined using the radioassays described in Example 1

(reaction batches: 9 μl of protein solution +1 μl of 1 mM [$^{14}$C]-N-acetyl-L-PPT, reaction conditions: see above). For the quantitative enzyme determination, the protein fractions were incubated at 37° C. with 50 mM of N-acetyl-D,L-PPT (9 μl of protein solution +1 μl of 500 mM N-acetyl-D,L-PPT) for 30 min. The resulting PPT was then measured in an amino acid analyzer (Biotronic LC 5001). The protein in the crude extract after cell disruption had a specific deacetylase activity of 3 ncat/mg of protein (1 ncat=1 nmol of substrate/sec.). From 800 ml of culture of the expression strain, it was possible by affinity chromatography to isolate 10 mg of HisTag deac fusion protein having a specific activity of 20 ncat/mg of protein and a purity of about 80%.

3. Substrate Specificity and Stereoselectivity of the Deacetylase

For the investigation of substrate specificity and stereospecificity of the deac1 protein, 5 μg each of purified enzyme were incubated in 20 μl batches in 10 mM NaCl, 10 mM Na phosphate, pH=7.5 with 25 mM each of the N-acetyl-L-amino acids or of the corresponding D enantiomers mentioned in Table 1. For comparison, hippuric acid (N-benzoylglycine), the natural substrate of deacetylase, was employed. The reactions were incubated at 37° C. for 1 h and then measured in the amino acid analyzer (Biotronic LC 5001) for formation of the free amino acids. Table 1 indicates the relative deacetylase activities for the L-enantiomers of the various substrates. In addition to hippuric acid and N-Ac-L-PPT, the deac1 enzyme also additionally cleaves the N-acetyl derivatives of a number of natural amino acids, in particular N-Ac-L-glutamic acid, N-Ac-glycine, N-Ac-L-histidine, N-Ac-L-ornithine, N-Ac-L-leucine, N-Ac-L-glutamine and N-Ac-L-phenylalanine. In all cases, the enzyme was exclusively active with the L enantiomers, while it was not possible to react the corresponding D compounds in any case. In all other cases tested (see Table 1), the reaction of the N-cetyl-L derivatives only took place to a very small extent or else not at all.

TABLE 1

Substrate specificity of the deac enzyme

| Substrate[1] | Rel. activity[2] [%] |
| --- | --- |
| Hippuric acid (N-benzoylglycine) | 100 |
| N-Ac-L-phosphinothricin | 43 |
| N-Ac-L-ornithine | 37 |
| N-Ac-L-methionine | 0 |
| N-Ac-L-tryptophan | 0.4 |
| N-Ac-L-phenylalanine | 24 |
| N-Ac-L-tyrosine | 11 |
| N-Ac-L-glutamic acid | 100 |
| N-Ac-L-glutamine | 30 |
| N-Ac-glycine | 59 |
| N-Ac-L-histidine | 43 |
| N-Ac-L-leucine | 33 |
| N-Ac-L-valine | 2 |
| N-Ac-L-serine | 4 |
| N-Ac-L-proline | 0 |

[1]All compounds are the L enantiomers
[2]The specific activity [nmol of glycine/min/mg of protein] measured using hippuric acid was set equal to 100%, and the other values were based thereon

4. Resolution of N-acetyl-D,L-phosphinothricin by Biotransformatibn Using Cells of the Deac Producer Strain A 400 ml culture of the expression strain pQEDEAC was fermented and induced as described in Example 1. The harvested cells were then washed in 10 mM NaCl, 10 mM Na phosphate, pH=7.5 and lyophilized overnight. It was possible to store the cells treated in this way for several weeks at 4° C. while maintaining a high specific deacetylase activity and to use them in the following experiments as a biocatalyst.

2 mg of the lyophilized cells were resuspended in 1 ml of the following substrate solutions of varying concentrations:

| | |
| --- | --- |
| (1) | 10 mM N-acetyl-D,L-PPT, disodium salt (0.3%) |
| (2) | 50 mM N-acetyl-D,L-PPT, disodium salt (1.3%) |
| (3) | 100 mM N-acetyl-D,L-PPT, disodium salt (2.6%) |
| (4) | 250 mM N-acetyl-D,L-PPT, disodium salt (6.7%) |
| (5) | 500 mM N-acetyl-D,L-PPT, disodium salt (13.3%) |

As reaction buffer, the batches contained 10 mM NaCl, 10 mM Na phosphate, pH=8.0 and were incubated on a shaker at 100 rpm and 37° C. for 48 h. The free PPT formed in the hydrolysis reaction was determined in an amino acid analyzer (Biotronic LC 5001). The results are summarized in Table 2. The enantiomeric purity of the reaction product was analyzed by chiral HPLC using the separating column Chirex® (D) Penicillamine (Phenomenex). The eluate used was 2 mM $CuSO_4$, 10% methanol with a flow rate of 0.5 ml/min. Detection was carried out photometrically at 254 nm. Under these conditions, reference solutions of L-PPT elute at 17 min and those of D-PPT at 21 min. In all test samples, L-PPT was detected exclusively as the reaction production. The conversion rates achieved [L-PPT produced/N-acetyl-L-PPT in the substrate×100] were between 100% in the low substrate concentrations (10 mM, 50 mM) and 66% in the highest substrate concentration used (500 mM).

TABLE 2

Resolution of N-acetyl-D,L-PPT as a function of the substrate concentration

| Substrate solution N-acetyl-D,L-PPT [mM] | Product solution* L-PPT [mM] | Conversion rate L-PPT/N-acetyl-D,L-PPT in % |
| --- | --- | --- |
| 10 | 5 | 100 |
| 50 | 25 | 100 |
| 100 | 48 | 96 |
| 250 | 108 | 86 |
| 500 | 164 | 66 |

*Concentration of biocatalyst: 2 mg/ml

In the following experiment, the concentration of biocatalyst was increased and reaction kinetics of the substrate cleavage were recorded. 13 mg of the lyophilized cells were resuspended in 1 ml of substrate solution, consisting of 500 mM N-acetyl-D,L-PPT, disodium salt (13.3% w/v), 10 mM NaCl, 10 mM Na phosphate, pH=8.0 and incubated at 100 rpm and 37° C. on a shaker. For the determination of the L-PPT formed, 50 μl each of aliquots from the reaction batch were removed over a period of 55 h, centrifuged and the supematants were frozen at −20° C. until analysis. The quantitative analysis of the reaction product L-PPT and the determination of the enantiomeric purity were carried out as described above. The results are summarized in Table 3. Under the chosen conditions, the L-specific substrate cleavage was complete after about 55 h. In this case, a conversion rate of about 90% and a space/time yield of 483 [mg of L-PPT/g of biocatalyst/h] were achieved.

TABLE 3

Reaction kinetics of the resolution of N-acetyl-D,L-PPT

| Reaction time [h] | L-PPT [mM]* |
|---|---|
| 0 | 0 |
| 1 | 27.7 |
| 4 | 59.7 |
| 9 | 106.0 |
| 23 | 181.6 |
| 31 | 186.5 |
| 47 | 208.6 |
| 55 | 221.8 |

*Concentration of biocatalyst: 13 mg/ml
Substrate concentration: 500 mM N-acetyl-D,L-PPT 5. Immobilization of the purified deac protein:

In order to be able to carry out the enzyme reaction with the isolated deac protein, the enzyme purified in Example 2 as a HisTag fusion protein was immobilized on the polymer carrier VINA-Epoxy Biosynth® (Riedel de Haen). For this, the deac protein was concentrated to 15 mg/ml by ammonium sulfate precipitation and dialyzed overnight against 1 M Na phosphate, pH=8.0. For a standard coupling reaction, 10 mg of the protein were slowly shaken at room temperature for 2 days with 100 mg of VINA carrier. The immobilizate was then centrifuged off and washed 1× each in immobilization buffer, and also in 50 mM Na phosphate, pH 7.0. To block free epoxy groups, the carrier was then incubated at room temperature with 50 mM Na phosphate, pH=7.0, 50 mM 2-mercapto-ethanol for 1 h. The biocatalyst was then stored at 4° C. in 1 ml of 5 mM Na phosphate, pH=7.0, 0.02% Na azide. For the determination of the protein coupling, the protein content of the solution was determined before and after immobilization, and also in the wash solutions, with the aid of the Bradford method [Bradford (1976), Anal. Biochem. 72 :248–254]. The specific activity of the deacetylase was measured before and after immobilization using the radioassay described in Example 1. After coupling, the relative enzyme activity was >90% of the value determined for the dissolved protein.

6. Resolution of N-acetyl-D,L-phosphinothricin Using Immobilized Deac Enzyme in a Column Reactor 1 g of enzyme immobilizate (moist weight) was loaded into a column reactor and used as a biocatalyst for the resolution of various concentrated substrate solutions having various flow rates. The substrate solutions contained the concentrations of N-acetyl-D,L-PPT, diammonium salt in 10 mM NaCl, 10 mM Na phosphate, pH=8.0 indicated in Table 4. The reactions were carried out at 37° C. for a total of 10 days. The reactions were quantified by determination of the L-PPT present in the material flowing through the column by means of amino acid analysis and chiral HPLC (see Example 4). The results are presented in Table 4. The highest conversion rate of 83% was achieved using the highest substrate concentrations (500 mM) and the lowest substrate flow (0.03 ml/min). The space/time yield increased with the flow rate and the substrate concentrations and reached the highest value of 181 [mg of L-PPT/g of biocatalyst/h] at a substrate concentration of 500 mM and a flow of 0.3 ml/min. Over the total experimental period, the immobilized deacetylase showed a good stability and still had about 80% of the starting activity after 10 days at 37° C.

TABLE 4

Resolution of N-acetyl-D,L-PPT using immobilized deac enzyme in a column reactor

| Substrate solution N-acetyl-D,L-PPT [mM] | Flow rate [ml/min.] | Product solution L-PPT [mM] | Conversion rate [%] | Space/time yield [mg of L-PPT/g of biocatalyst/h]* |
|---|---|---|---|---|
| 100 | 0.1 | 29.7 | 59 | 39 |
|  | 0.3 | 22.0 | 44 | 87 |
|  | 0.5 | 13.8 | 28 | 91 |
| 250 | 0.1 | 38.4 | 31 | 50 |
|  | 0.3 | 25.0 | 20 | 99 |
|  | 0.5 | 18.1 | 14 | 119 |
| 500 | 0.1 | 71.1 | 28 | 93 |
|  | 0.3 | 46.0 | 18 | 181 |
|  | 0.5 | 26.3 | 11 | 173 |
| 500 | 0.03 | 208.2 | 83 | 82 |

*Reactions at 37° C.

What is claimed is:

1. A process for the preparation of proteinogenic or nonproteinogenic L-amino acids form their racemic N-acetyl-D,L-derivatives, which comprises:

(a) employing racemic N-acetyl-D,L-derivatives at a concentration of from 50 mM to 1500 mM;

(b) selectively deacetylating N-acteyl-L-derivatives of the corresponding L-amino acids by an enzymatic resolution utilizing isolated, recombinant hippurate hydrolases, while N-acetyl-D-derivatives of the corresponding D-amino acids are not deacetylated; and (c) separating the deacetylated L-amino acids obtained preparatively from the nondeacetyalted N-actyl-D-derivatives and/or incompletely deactylated N-actyl-L-derivatives.

2. The process as claimed in claim 1 for the preparation of L-phosphinothricin (L-PPT) from racemic N-acetyl-D,L-phosphinothricin.

3. The process as claimed in claim 1 for the preparation of L-glutamic acid, L-histidine, L-leucine, L-glutamine and/or L-phenylalanine from their corresponding N-acetyl-D,L derivatives.

4. The process as claimed in claim 1, wherein the enantioselective production of one or more L-amino acids form their corresponding racemic N-acetyl-D,L derivatives is carried out using the enzymes deac1 from *Stenotrophomonas sp.* and/or deac2 from *Comamonas acidovorans*.

5. The process as claimed in claim 1, wherein the enantioselective production of L-phosphinothricin, L-glutamic acid, L-histidine, L-leucine, L-glutamine, and/or L-phenylalanine from their corresponding racemic N-acetyl-D,L derivatives is carried out using the enzymes deac1 from *Stenotrophomonas sp.* and/or deac2 from *Comamonas acidovorans*.

6. The process as claimed in claim 1, wherein the recombinant deacetylases produced are employed in immobilized form.

7. The process as claimed in claim 1, wherein the reaction temperatures are approximately 25° C. to 65° C.

8. A method for the enantioselective production of one or more L-amino acids from their corresponding N-acetyl-D,L derivatives, comprising the step of utilizing one or more isolated, recombinant hippurate hydrolases and the subsequent separation of the L-amino acids from incompletely deacetylated N-acetyl-L-amino acids and from non-deacetylated N-acetyl-L-amino acids.

9. A method for the enantioselective production of L-phosphinothricin, L-glutamic acid, L-histidine, L-leucine, L-glutamine and/or L-phenylalanine from their corresponding N-acetyl-D,L derivatives, comprising the step of utilizing one or more isolated, recombinant hippurate hydrolases and the subsequent separation of the L-amino acids from incompletely deacetvlated N-acetyl-L-amino acids and from non-deacetylated N-acetyl-L-amino acids.

10. A method for the enantioselective production of one or more L-amnino acids from their corresponding racemic N-acetyl-D,L derivatives, comprising the step of utilizing isolated, recombinant deac1 from *Stenotrophomonas sp.* and/or deac2 from *Comamonas acidovorans* and the subsequent separation of the L-amino acids from incompletely deacetylated N-acetyl-L-amino acids and from non-deacetylated N-acetyl-L-amino acids.

11. A method for the enantioselective production of L-phosphinothricin, L-glutamic acid, L-histidine, L-leucine, L-glutamine, L-phenylalanine from their corresponding racemic N-actyl-D,L derivatives, comprising the step of utilizing isolated, recombinant deac1 from *Stenotrophomonas sp.* and/or deac2 from *Comamonas acidovorans* and the subsequent separation of the L-amino acids from incompletely deacetylated N-acetyl-L-amino acids and from non-deacetylated N-acetyl-L-amino acids.

* * * * *